US006656311B2

(12) United States Patent
Venturino et al.

(10) Patent No.: US 6,656,311 B2
(45) Date of Patent: Dec. 2, 2003

(54) APPARATUS AND PROCESS FOR CONVERTING ASYMMETRICALLY NESTED ABSORBENT WEBS

(75) Inventors: Michael Barth Venturino, Appleton, WI (US); David Willis Heyn, Neenah, WI (US); Leon Robert Flesburg, Neenah, WI (US); Mark Charles Jacobs, Appleton, WI (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 232 days.

(21) Appl. No.: 09/975,103

(22) Filed: Oct. 10, 2001

(65) Prior Publication Data
US 2003/0066597 A1 Apr. 10, 2003

(51) Int. Cl.[7] .............................................. B32B 31/08
(52) U.S. Cl. ....................... 156/259; 156/256; 156/264; 156/271
(58) Field of Search ................................ 156/256, 259, 156/264, 266, 269, 271, 157, 163, 164

(56) References Cited

U.S. PATENT DOCUMENTS

| 3,072,123 A | | 1/1963 | Davis | |
|---|---|---|---|---|
| 3,488,778 A | | 1/1970 | Goujon et al. | |
| 3,759,262 A | * | 9/1973 | Jones, Sr. | 604/365 |
| 3,878,283 A | | 4/1975 | Jones, Sr. | |
| 4,464,217 A | * | 8/1984 | Dickover et al. | 156/164 |
| 4,862,574 A | | 9/1989 | Seidy | |
| 5,580,411 A | | 12/1996 | Nease et al. | |
| 5,597,437 A | | 1/1997 | Lange et al. | |
| 5,695,846 A | | 12/1997 | Lange et al. | |
| 5,826,475 A | * | 10/1998 | Mysliwiec | 83/116 |

FOREIGN PATENT DOCUMENTS

| EP | 0 280 998 A1 | | 7/1988 |
|---|---|---|---|
| EP | 0 539 032 B1 | | 4/1993 |
| EP | 0 625 602 B1 | | 11/1994 |
| EP | 0 670 153 B1 | | 9/1995 |
| FR | 2 209 520 | | 5/1974 |
| GB | 1217402 A | * | 12/1970 |

* cited by examiner

Primary Examiner—Jeff H. Aftergut
(74) Attorney, Agent, or Firm—Paul Yee; John L. Brodersen

(57) ABSTRACT

A method and apparatus (20) for making an absorbent article can include a delivering of a first contoured web-strip (30a) from a first production supply (38) of contoured web-strip material, with the first contoured web-strip (30a) presenting a primary production sequence of side edge contours during its delivery. At least a second contoured web-strip (30b) can be delivered from a second production supply (40) of the contoured web-strip material, with the second contoured web-strip (30b) also presenting the primary production sequence of side edge contours during its delivery. In a particular aspect, the first and second contoured web-strips (30a and 30b) have been produced from a web (22) of absorbent material which has been divided to provided at least two web-strips (30) having a substantially nested configuration. In another aspect, the first web-strip (30a) provides a first orientation which presents a first sequence of side edge contours; and the second web-strip (30b) provides a longitudinally-reversed orientation which presents a different, substantially reversed sequence of side edge contours. In an additional aspect, the web-strips (30) have been separately stored to provide the first and second production supplies (38, 40) of contoured web-strip material.

20 Claims, 5 Drawing Sheets

APPARATUS AND PROCESS FOR CONVERTING ASYMMETRICALLY NESTED ABSORBENT WEBS

FIELD OF THE INVENTION

This invention generally relates to apparatus and method for forming an absorbent web. In particular configurations, the apparatus and method can substantially continuously deliver an absorbent web having side edges that have been shaped with a contour pattern that is asymmetric along a lengthwise dimension of the shaped web. The shaped, absorbent web can be employed to produce an absorbent pad for applications such as disposable diapers, child's training pants, feminine care articles, incontinence articles, and the like.

BACKGROUND OF THE INVENTION

In the general practice of forming absorbent web materials, the webs have been formed by employing conventional airlaying techniques. For example, it has been common to utilize a fibrous sheet of cellulosic or other suitable absorbent material which has been fiberized in a conventional fiberizer, or other shredding or comminuting device, to form discrete fibers. In addition, particles of superabsorbent material have been mixed with the discrete fibers. The fibers and superabsorbent particles have then been entrained in an air stream and directed to a foraminous forming surface upon which the fibers and superabsorbent particles have been deposited to form an absorbent fibrous web. The absorbent web can then be directed for further processing and assembly with other components to produce a final absorbent article.

In other ordinary techniques, preformed absorbent sheets or layers have been delivered into a manufacturing line from an operative preformed supply, such as provided by a supply roll. The preformed absorbent sheets have been composed of absorbent fibers, synthetic fibers and superabsorbent materials in desired combinations. In particular, manufacturing processes, the preformed absorbent sheets have been separated into adjacent strips having various configurations of "nested" shapes. The preformed absorbent materials can be expensive, and the nested shapes have been employed to reduce any wastage of the preformed sheet material. The strips of absorbent material may then be assembled together in various ways and combined with other components to generate a desired absorbent article.

Conventional techniques, such as those described above, have continued to exhibit various shortcomings when employed to form absorbent structures from preformed layers of absorbent material. For example, with the conventional techniques, it has been difficult to fully utilize the adjacent, shaped strips of nested absorbent material when the nested-shapes of the absorbent strips have a contoured repeat-pattern that is non-symmetric with respect to longitudinal, lengthwise dimension of the strips. Where the repeat-pattern is longitudinally asymmetric, a single cycle of the repeat-pattern of one shaped-strip can be longitudinally reversed, as compared to a single cycle of the repeat-pattern of an immediately adjacent shaped-strip. As a result, it has been difficult to efficiently use the immediately adjacent, shaped-strips on a single manufacturing line. For example, it has been difficult to serially connect the immediately adjacent, shaped-strips, and use the connected strips on a manufacturing line having a pre-established sequence of assembly operations. It has also been difficult to superpose portions of immediately adjacent, shaped-strips during an inline process because the adjacent strips have non-matching shapes. Accordingly, it would be a substantial advance in the art to provide a method and apparatus which can provide a more efficient handling and use of adjacent, nested strips which have been separated from a supply sheet, wherein the separated edges represent a repeat-pattern having a pattern shape that is non-symmetric with respect to the lengthwise dimension of the strips.

BRIEF DESCRIPTION OF THE INVENTION

A method and apparatus for making an absorbent article can include a delivering of a first contoured web-strip from a first production supply of contoured web-strip material, with the first contoured web-strip presenting a primary production sequence of side edge contours during its delivery. At least a second contoured web-strip can be delivered from a second production supply of the contoured web-strip material, with the second contoured web-strip presenting the primary production sequence of side edge contours during its delivery. In a particular feature, the first and second contoured web-strips have been produced from a web of absorbent material which has been divided to provide at least two web-strips having a substantially nested configuration. In another feature, the first web-strip can provide a first orientation which presents a first sequence of side edge contours; and the second web-strip can provide a longitudinally-reversed orientation which presents a different, substantially reversed sequence of side edge contours. In an additional feature, the web-strips have been separately stored to provide the first and second production supplies of contoured web-strip material.

By incorporating the various aspects and features into desired configurations, the present invention can more efficiently use the immediately adjacent, shaped-strips that have been formed in a nested configuration with a repeat-pattern shape that is longitudinally asymmetric. For example, the invention can more efficiently connect the immediately adjacent, shaped-strips in series, and use the connected strips on a manufacturing line having a pre-established sequence of assembly operations. The invention can also more efficiently superpose selected portions of immediately adjacent, shaped-strips onto each other during an inline process because the adjacent strips have substantially matching shapes. Accordingly, the technique of the present invention can provide a more efficient handling and use of adjacent, nested strips when the nested strips have been separated from a supply web in a manner which provides a contoured repeat-pattern having a single-cycle pattern shape that is non-symmetric with respect to the lengthwise dimension of the strips.

BRIEF DESCRIPTION OF THE DRAWINGS

The invention will be more fully understood and further advantages will become apparent when reference is made to the following detailed description of the invention and to the drawings in which.

DETAILED DESCRIPTION OF THE INVENTION

Figure 1:
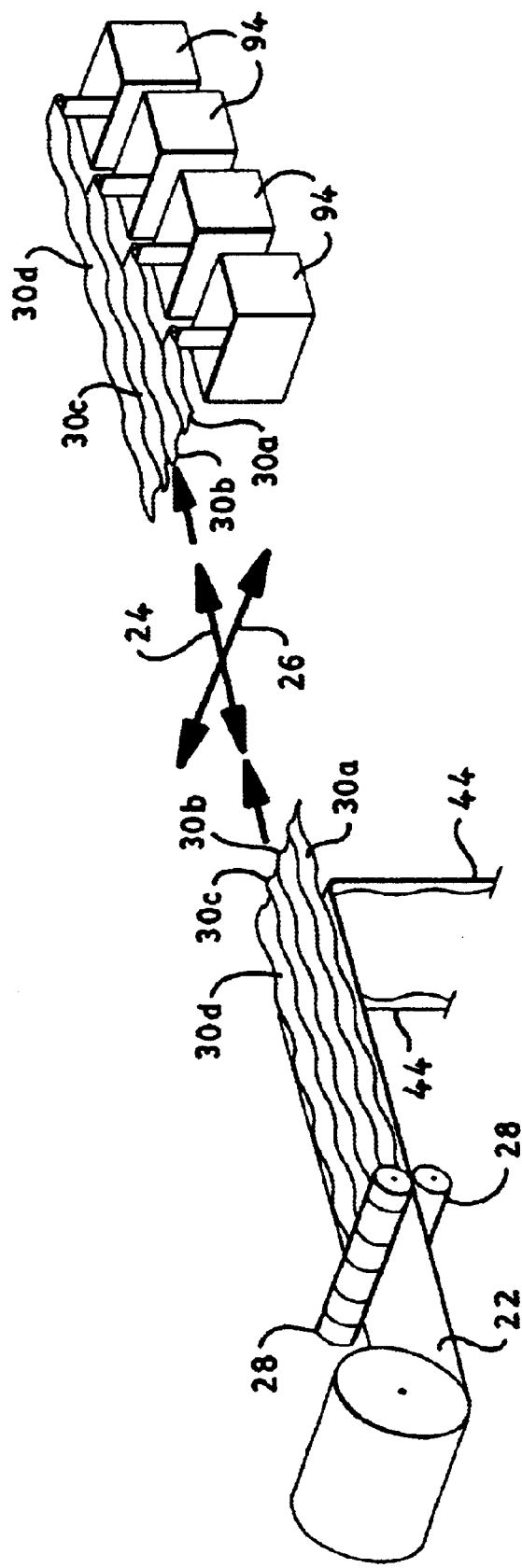
FIG. 1 shows a schematic view of a representative method and apparatus which can separate an absorbent web along a plurality of serpentine division lines to provide a plurality of absorbent web-strips.

Preformed absorbent webs have typically been stored by employing conventional storage/supply systems, such as provided by supply rolls. The preformed absorbent webs have been cut or otherwise separated into side-by-side strips, and the strips have been configured with selected repeat-pattern shapes wherein the shape of one strip is substantially nested with the shaped of at least one immediately adjacent strip. In a particular feature the shape of one strip can be substantially nested with a pair of immediately adjacent strips. The nesting of the adjacent strips has been desirable to reduce the amount of waste that is generated from the originally supplied web of absorbent material. It has been known that particular nested strips-shapes can be more readily adapted to high-speed manufacturing operations. The more easily processed strip-shapes have a repeat-pattern shape that is substantially symmetrical with respect to its longitudinal, machine-direction. With such longitudinally-symmetric nested patterns, a single cycle of the repeat-pattern can provide an individual web-segment shape wherein the shape of a first lengthwise half-portion of the web segment substantially matches the shape of the longitudinally opposed, second half-portion of that web segment.

An individual web-segment is typically employed to construct an absorbent pad structure for an individual article. When employing web-segments with geometries that are longitudinally-symmetric, however, the resulting absorbent pads have not sufficiently provided desired levels of product fit, comfort and performance.

As a result, it has been desirable to construct an absorbent pad by employing a web-segment that is longitudinally-asymmetric. With such constructions, the resulting absorbent pad structure can provide improved product fit, comfort and performance. The dividing of an absorbent web into web-strips having a nesting repeat-pattern shape that provides the desired longitudinally asymmetric web-segments, however, has created significant problems. In particular, the shape-sequence in a first web-strip is typically reversed with respect to the shape-sequence exhibited by an immediately adjacent web-strip. Thus, when multiple web-strips are formed from the parent absorbent web, the resulting web-strips have exhibited an alternating, lane geometry. In odd-numbered lane or deckle positions, the web-segments will be configured to present a first end-shape that leads a second end-shape. In even-numbered lane or deckle positions, the web-segments will be configured to present a first end-shape that trails the second end-shape.

The alternating lane geometry has caused excessive complexity when the differing web-strips are delivered to a high-speed manufacturing operation. For example, when web-strips are wound onto a storage roll and then unwound into a converting process, every other roll of web-strip material is orientated backwards relative to the "front" and "back" sequencing of the desired absorbent pad structure. It has not been acceptable to have the entire converting process switch its production timing and registration-control to accommodate the reversed presentation of the web-segment shape when differing web-strips are spliced together during a conventional high-speed operation. Further, it has been impractical to set up two different manufacturing lines with each manufacturing line dedicated to a single orientation and presentation sequence of the supplied web-strip. As a result, there has been a continued need for improved methods and apparatus for processing webs that include longitudinally-asymmetric web-segments. Such improved methods and apparatus can advantageously be provided by the present disclosure.

It should be noted that, when employed in the present disclosure, the terms "comprises", "comprising" and other derivatives from the root term "comprise" are intended to be open-ended terms that specify the presence of any stated features, elements, integers, steps, or components, and are not intended to preclude the presence or addition of one or more other features, elements, integers, steps, components, or groups thereof.

The method and apparatus of the invention can be configured to produce various types of desired absorbent articles. Such articles can include, for example, infant diapers, children's training pants, feminine care articles, adult incontinence garments, and the like. The articles may be disposable, and intended for limited use. Typically, the disposable articles are not intended for washing and reuse.

Figure 2:
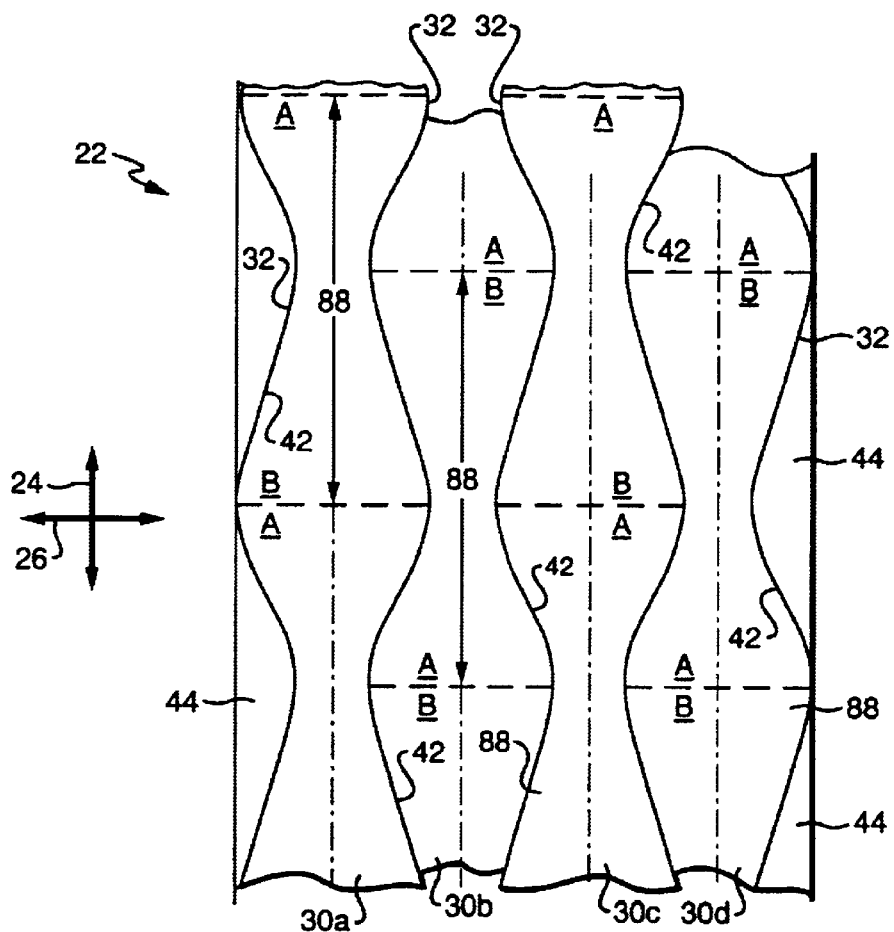
FIG. 2 shows a representative, top view of an absorbent web which has been separated along a plurality of division lines to provide a plurality of absorbent web-strips having transversely-shaped side margins configured to provide an interconnected series of designated web-segments.
Figure 5:
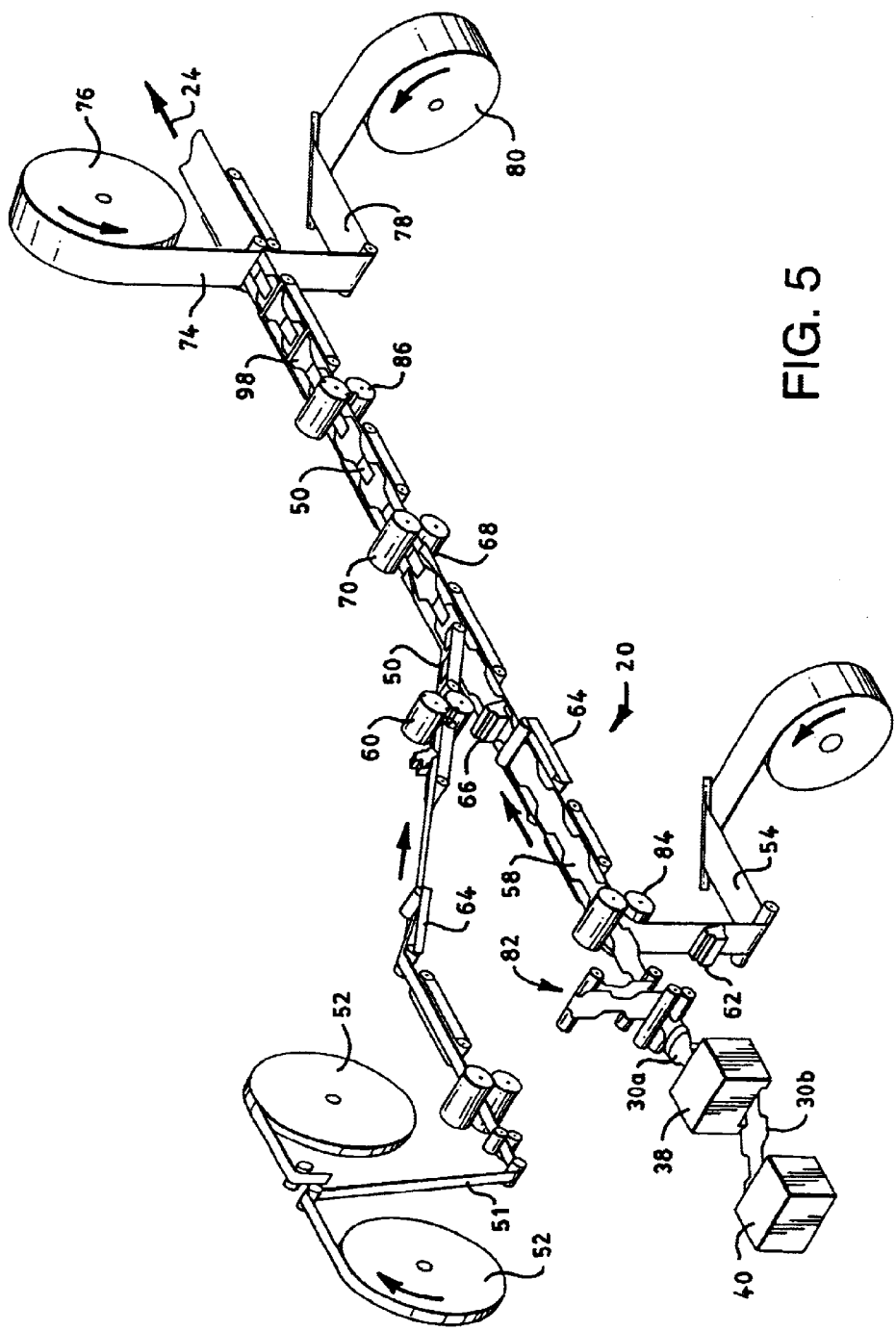
FIG. 5 representatively shows a schematic, perspective view of a method and apparatus that can incorporate the present invention.

With reference to FIGS. 1, 2 and 5, the process and apparatus of the invention can have a lengthwise, machine-direction 24 which extends longitudinally, a lateral cross-direction 26 which extends transversely, and a z-direction. For the purposes of the present disclosure, the machine-direction 24 is the direction along which a particular component or material is transported length-wise along and through a particular, local position of the apparatus and method. The cross-direction 26 lies generally within the plane of the material being transported through the process, and is aligned perpendicular to the local machine-direction 24. The z-direction is aligned substantially perpendicular to both the machine-direction 24 and the cross-direction 26, and extends generally along a depth-wise, thickness dimension.

As illustrated in FIGS. 1, 2 and 5, a representative method and apparatus 20 for making an absorbent article can include a delivering of a first contoured web-strip 30a from a first production supply 38 of contoured web-strip material, with the first contoured web-strip 30a presenting a primary production sequence of side edge contours during the delivering of the first contoured web-strip. At least a second contoured web-strip 30b can be delivered from a second production supply 40 of the contoured web-strip material, and the second contoured web-strip 30b can also present the primary production sequence of side edge contours during the delivering of the second contoured web-strip 30b. In a particular aspect, the first and second contoured web-strips 30a and 30b have been produced from a web 22 of absorbent material. The web 22 of absorbent material has been divided to provided at least two web-strips 30 having a substantially nested configuration. Each web-strip can have a pair of laterally opposed contoured side edges 32 with alternating, concave and convex side edge portions 34 and 36, respectively. In another aspect, the first web-strip 30a has been configured to provide a first orientation which presents a first sequence of side edge contours; and at least a second web-strip 30b has been configured to provide a longitudinally-reversed orientation which presents a different, substantially reversed sequence of side edge contours. In an additional aspect, the web-strips 30 have been separately stored to provide the first production supply 38 of contoured web-strip material, and at least the second production supply 40 of contoured web-strip material.

In another aspect, the method and apparatus 20 for making an absorbent article can include a providing of a web 22 of absorbent material, and a dividing of the web 22 to provide at least two web-strips 30 having a substantially nested relation. Each of the web-strips 30 can have a pair of laterally opposed, contoured side edges 32 with alternating, concave and convex side edge portions 34 and 36, respectively. A first web-strip 30a can be configured to provide a first orientation which presents a first sequence of side edge contours, and at least a second web-strip 30b can be configured to provide a longitudinally-reversed orientation which presents a different, substantially reversed sequence of side edge contours 32. The web-strips can be separately stored to provide a first production supply 38 of contoured web-strip material, and at least a second production supply 40 of contoured web-strip material. A first contoured web-strip 30a can be delivered from the first production supply 38 of contoured web-strip material, the first contoured web-strip material presenting a primary production sequence of side edge contours during the delivering of the first contoured web-strip 30a. At least a second contoured web-strip 30b can be delivered from the second production supply 40 of contoured web-strip material, the second contoured web-strip 30b presenting the primary production sequence of side edge contours during the delivering of the second contoured web-strip 30b.

Figure 3:
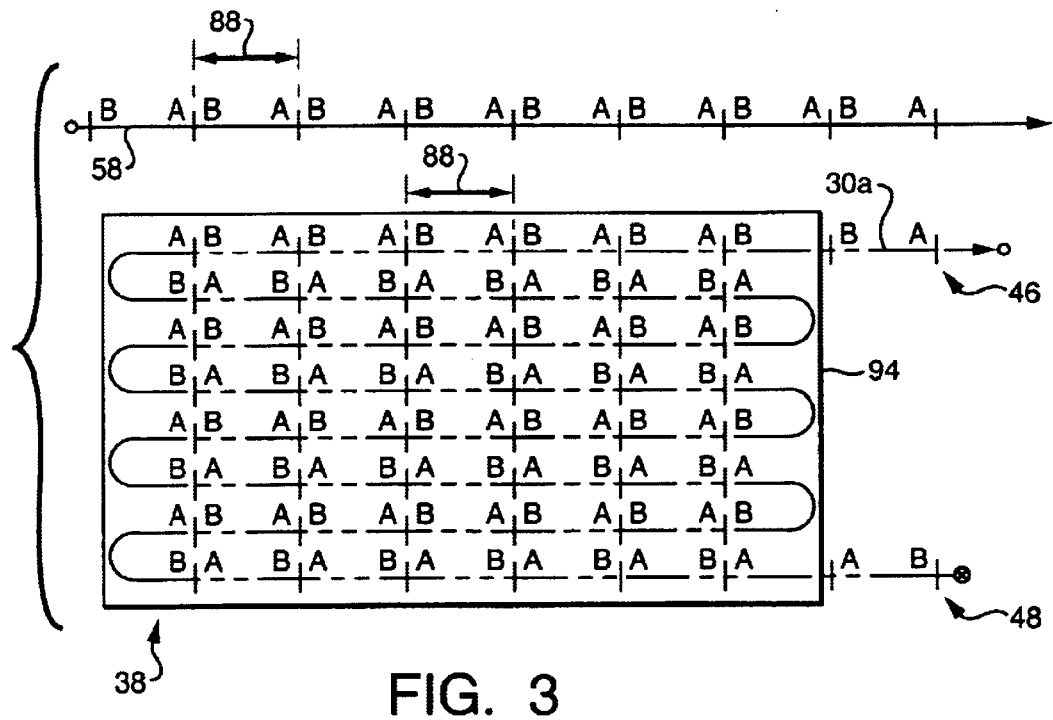
FIG. 3 shows a schematic, side view of a representative container that is configured to deliver a primary-order web-strip in a manner that matches a desired shape sequence presented along a base web.
Figure 3A:
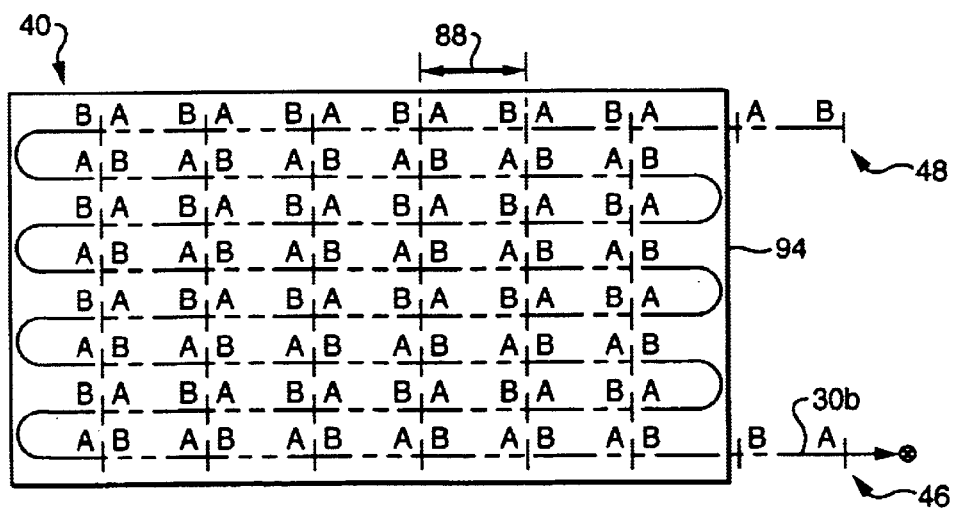
FIG. 3A shows a schematic, side view of another representative container that is configured to deliver a reverse-order web-strip in a manner that matches the shape sequence presented along the base web.

In a further feature of the invention can include a splicing or other operative joining of a leading-end portion 46 of the second contoured web-strip 30b to a trailing-end portion 48 of the first contoured web-strip 30a to provide a continuing base web 58 (e.g. FIGS. 3 and 3A). In another feature, the concave side edge portions 34 can be configured to be non-symmetric with respect to a longitudinal machine-direction 24 of the base web 58. In an additional feature, the convex side edge portions 36 can be configured to be non-symmetric with respect to the longitudinal, machine-direction 24 of the base web 58.

By incorporating the various aspects and features into desired configurations, the present invention can more efficiently use the immediately adjacent, shaped-strips that have been formed in a nested configuration with a periodic, repeat-pattern shape that is longitudinally asymmetric. For example, the invention can more efficiently connect the immediately adjacent, shaped-strips in series, and use the connected strips on a manufacturing line having a pre-established configuration of assembly operations. The invention can also more efficiently superpose selected portions of immediately adjacent, shaped-strips onto each other during an inline process because the adjacent strips have substantially matching shapes. Accordingly, the technique of the present invention can provide a more efficient handling and use of adjacent, nested strips when the nested strips have been separated from a supply web in a manner which provides a contoured, periodic repeat-pattern having a single-cycle pattern shape that is non-symmetric with respect to the lengthwise dimension of the strips. The technique of the invention can more efficiently form an absorbent web into desired shapes with less waste and less expense. A manufacturing operation which incorporates the technique is not limited to rectangular or other symmetrically shaped absorbent pads, and is better able to produce pads that provide improved fit and comfort.

With reference to FIGS. 1, 3, 3A and 5, the selected, absorbent web material can be introduced into the system by any operative delivery from a suitable supply of the web material. For example, the absorbent material may be delivered from a supply roll, or may optionally be supplied from an inline manufacturing operation.

The absorbent web may include cellulosic fibers (e.g., wood pulp fibers), other natural fibers, synthetic fibers, woven or nonwoven sheets, scrim netting or other stabilizing structures, superabsorbent material, binder materials, surfactants, selected hydrophobic materials, pigments, lotions, odor control agents or the like, as well as combinations thereof.

Superabsorbent materials are well known in the art, and are readily available from various suppliers. For example, FAVOR 880 superabsorbent is available from Stockhausen, Inc., a business having offices located in Greensboro, N.C., U.S.A.; and DOW 2035 is available from Dow Chemical Company, a business having offices located in Midland, Mich., U.S.A.

The absorbent materials may be integrated into the absorbent web by employing any operative method or apparatus. For example, the absorbent web may be formed with a dry-forming technique, an airlaying technique, a wet-forming technique, a foam-forming technique or the like, as well as combinations thereof. Methods and apparatus for carrying out such techniques are well known in the art.

In a particular aspect of the invention, the web 22 of absorbent material can be provided with an absorbent capacity of at least a minimum of about 8 g/g employing 0.9 wt % saline (8 grams of 0.9 wt % saline per gram of absorbent web). The absorbent capacity of the absorbent web can alternatively be at least about 9 g/g, and can optionally be at least about 10 g/g to provide improved benefits. Additionally, the absorbent capacity may be up to about 50 g/g, or more, to provide desired performance.

In another aspect, the web of absorbent material can be provided with a tensile strength value of at least a minimum of about 1 N/cm (Newtons per cm of "width" of the material, where the "width" direction is perpendicular to the applied force). The tensile strength of the absorbent web can alternatively be at least about 1.5 N/cm, and can optionally be at least about 2 N/cm to provide improved benefits.

In another aspect, the web of absorbent material can be provided with a tensile strength value of up to a maximum of about 100 N/cm, or more. The tensile strength of the absorbent web can alternatively be up to about 20 N/cm, and can optionally be up to about 10 N/cm to provide improved benefits.

The selected tensile strength can, for example, provide improved processibility through the manufacturing process and apparatus. Additionally, the selected tensile strength can help to produce articles that exhibit desired combinations of softness and flexibility during ordinary use.

With reference to FIGS. 1, 2, 2A and 4, a web 22 of absorbent material can be delivered from a web supply, and can be transported with a conventional conveyor system to an operative, web cutter 28. Suitable cutter mechanisms and devices are well known in the art, and can include rotary knives, die cutters, water-cutters, lasers and the like, as well as combinations thereof. The web cutter can divide the absorbent web material to form a first web-strip 30a and at least a second web-strip 30b. In other configurations, the invention can be arranged to provide additional web-strips, such as web-strips 30d and 30d. Additional web-strips may also be provided, as desired.

As representatively shown, a cooperating plurality of serpentine dividing lines 42 can be employed to separate the precursor, parent web 22 into a plurality of two or more, contoured, nested web-strips 30. With the nested configuration of the web-strips, the amount of trim wastage 44 can be reduced. Each dividing line undulates with a cyclic, periodically repeating pattern, and adjacent pairs of the dividing lines are cooperatively arranged to provide the desired series of longitudinally-asymmetric web-segments 88 within each web strip.

Figure 2A:
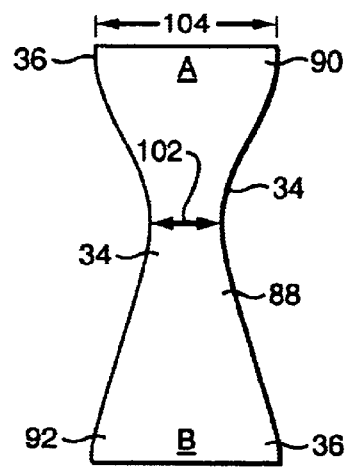
FIG. 2A shows a representative, individual web-segment.
Figure 4:
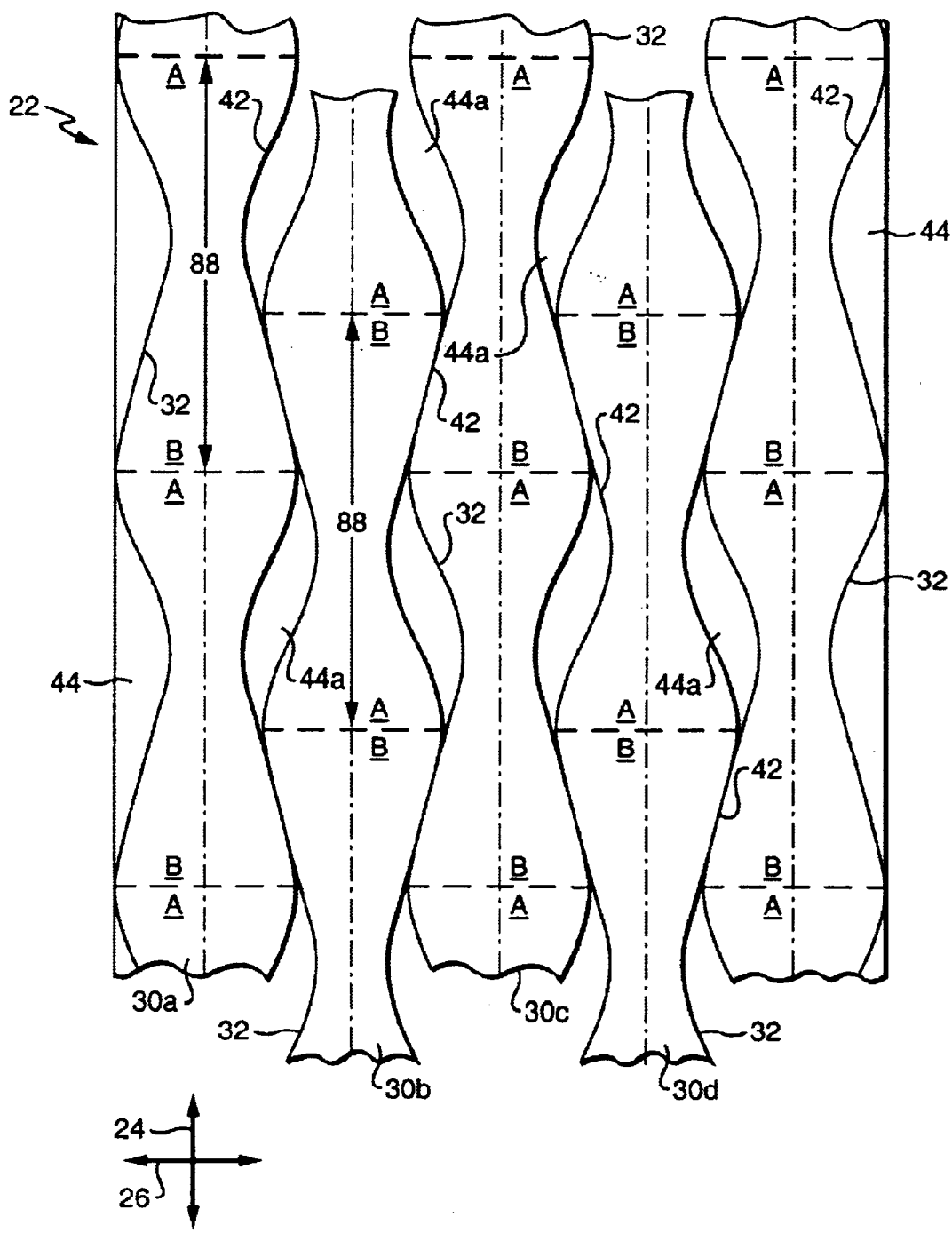
FIG. 4 shows a representative, top view of an absorbent web which is divided in a manner that produces trim-waste between adjacent web-strips.

With reference to FIGS. 2, 2A and 4, each web-strip 30 can include a laterally opposed pair of contoured side edges 32. Each contoured side edge can include a concave side edge portion 34 and a convex side edge portion 36. Each contoured side edge can be observed to undulate from side-to-side in the lateral direction 26 as one moves along the longitudinal direction 24 of the contoured side edge. Additionally, each web-strip 30 can be configured to be at least approximately nested with either or both of its immediately adjacent web-strips. In a desired configuration, each web-strip 30 can be configured to be substantially perfectly nested with either or both of its immediately adjacent web-strips. As representatively shown, for example, web-strip 30a can substantially nest with its immediately adjacent web-strip 30b. Additionally, web-strip 30b can substantially nest with both of the immediately adjacent web-strips 30a and 30c. As illustrated in the example of the representatively shown arrangement, alternating pairs of the web-strips (e.g. 30a–30c; 30b–30d) can have contoured shapes which are substantially identically presented. Accordingly within each alternating pair of web-strips, one web-strip has a presentation order of different web-segment, end-shapes which substantially matches a presentation order of such end-shapes in the other web-strip.

As illustrated in FIG. 4, the web-strips need not be perfectly nested with substantially zero waste trim between immediately adjacent web strips. Accordingly, there may a small amount of waste trim 44a between immediately adjacent web strips. The between-strip waste may be arranged in segregated areas, in contiguous areas or in combinations thereof. In a particular aspect, the area-amount of between-strip waste can be up to a maximum of about 30% of the projected area of an individual web-segment 88. The amount of between-strip waste can alternatively be up to about 25%, and optionally can be up to about 20%, of the area of an individual web-segment. To determine the percentage of between-strip waste, the area-amount of between-strip waste that is immediately adjacent a single, side-edge contour of a single web-segment is employed for the calculation.

With reference to FIGS. 2, 2A and 4, each web-strip 30 can provide an interconnected plurality of appointed web segments 88. The web-segments are typically designated or otherwise identified for separation from their corresponding web-strip during another operation. In the illustrated configuration, for example, the web-segments are separated from the web-strip in a subsequent cutting operation. Each web segment 88 can, for example, be configured to provide an absorbent component in an individual absorbent article. In a particular aspect, each web segment can be configured to provide a desired, individual total absorbency. The total absorbency can be varied, depending upon the intended end-user. For infant care products the total absorbency can be within the range of about 300–900 grams of 0.9 wt % saline, and can typically be about 500 g of saline. For adult care products, the total absorbency can be within the range of about 1000–1600 grams of saline, and can typically be about 1300 g of saline. For feminine care products, the total absorbency can be within the range of about 7–50 grams of saline, and can typically be within the range of about 30–40 g of saline.

In another aspect, one end portion of each web-segment can be designated for placement at a "front" end of an absorbent pad structure, and an longitudinally opposite, second end portion of the web-segment can be designated for placement at a "back" or "rear" end or waistband portion of the absorbent pad. Additionally, a relatively narrowest, intermediate portion of the web-segment may be designated for placement at a "crotch" region of the absorbent pad. Accordingly, each web-segment can have a minimum crotch width dimension 102 and maximum waistband width dimension 104. The ratio of the waist-bandwidth to the crotch-width can be at least a minimum of about 1.5:1. The waistband to crotch width ratio can alternatively be at least about 2:1, and can optionally be about 3:1. Additionally, the waistband to crotch width ratio can be up to about 10:1 to provide desired levels of fit and performance.

In a further feature, the crotch width of the web-segment 88 can be tailored for each desired end product. For example, in a web-segment designated for a feminine care article, the crotch width can be within the range of about 2–5 cm. In a particular feminine care configuration, the crotch width can be about 3.8 cm (about 1.5 inch). For a web-segment designated for an infant care article, the crotch width can be within the range of about 4–12 cm. In a particular infant care configuration, the crotch width can be about 10 cm (about 4 inch). For a web-segment designated for an adult care article, the crotch width can be within the range of about 7–20 cm. In a particular adult care configuration, the crotch width can be about 15 cm (about 6 inch).

As representatively shown, the individual web-strips 30 can each have a bilateral symmetry with respect to the lateral, cross-direction of the web-strips. Accordingly, each appointed or designated web-segment 88 can have a bilateral symmetry with respect to the lateral, cross-direction of the web-segment. Additionally, the web-strips 30 can have nesting geometries which are configured to provide web-segments 88 that exhibit a selected longitudinal-asymmetry. With the longitudinally-asymmetric geometries, the adjacently nested strips have a shape repeat-pattern which is substantially non-symmetric with respect to its longitudinal, machine-direction. In such longitudinally-asymmetric, nested patterns, a single cycle of the periodic repeat-pattern can provide substantially the same predetermined shape to each successive web-segment within a web-strip. In each predetermined shape, however, the shape of a first lengthwise half-portion of the web segment does not match the shape of the longitudinally opposed, second half-portion of that web segment.

As representatively shown in FIGS. 2, 2A, 3, 3A and 4, the web-strips 30 can be configured to provide a periodic series of web segments 88 which are non-symmetric along their longitudinal direction 24. Accordingly, the shape (A) of a first end portion 90 of the web segment 88 can differ from the shape (B) of a second, longitudinally-opposed end portion 92 of that web segment. As a result, the first web-strip 30a can provide a first lengthwise orientation which presents a first sequence of the selected, laterally undulating sequence of the side edge contours 32.

Additionally, the first web-strip 30a can provide a first lengthwise orientation which presents a first sequence of contoured, end-region shapes (e.g. A-B, A-B, . . . ), as provided by the corresponding series of web segments 88 in the first web-strip.

The second web-strip can be provided by an immediately adjacent web-strip (e.g. web-strip 30b), or another alternate-lane web-strip that matches the sequence of contours and contour shapes that are serially presented by the adjacent web-strip. The selected second web-strip can provide a longitudinally-reversed orientation which presents a different, substantially reversed sequence of the laterally undulating side edge contours 32. Accordingly, a concave side edge portion 34 of the first web-strip 30a can be positioned adjacent a convex side edge portion 36 of the second web-strip 30b, and can be substantially nested therewith. Similarly, the convex side edge portions 36 of the first web-strip 30 can be positioned adjacent the concave side edge portions 34 of the second web-strip 30b, and substantially nested therewith. The concave side edge portions 34 of the other web-strips can be similarly positioned adjacent the convex side edge portions 36 of one or more adjacent web-strips. As a result, the second web-strip 30b can provide a second lengthwise orientation which presents a reversed sequence of the end-region shapes (e.g. B-A, B-A, . . . ) provided by the corresponding series of web segments in the second web-strip.

The separate storing of the first web-strip 30a can include a spiral winding of the first web-strip. The separate storing of the second web-strip 30b by spiral winding, however, has created problems. When the web-strip (e.g. 30a) from an odd-numbered lane is wound to form a roll, the first end shape (A) of each web-segment leads the different, second end shape (B) of the web-segment into the winding process. When these odd-numbered lanes are unwound, the first end shape (A) trails the second end shape (B).

When the web-strip (e.g. 30b) from an even-numbered lane is wound, however, the first end shape (A) of each web-segment trails the second end shape (B) of the web-segment into the winding process. When these even-numbered lanes are unwound, the first end shape (A) leads the second end shape (B). Changing the direction of the roll rotation (clockwise versus counter-clockwise) during the unwinding of a particular web-strip does not change the presentation order of the end shapes of the web-segments, with respect to which end shape is presented in a "leading" position. It is readily apparent that changing the rotation direction only changes which major surface of the web-strip is facing "up". With either direction of unwind-rotation of a web-strip roll, the unwinding process provides the same serial order and the same presentation sequence of the ends of the web-segments.

To address the sequencing differences that can be produced by the winding of differently sequenced web-strips, the separated storing of the second web-strip 30b can include a primary spiral winding of the second web-strip 30b; and a subsequent, supplemental spiral re-winding of the second web-strip 30b to thereby provide the second production supply 40 of web material. The supplemental rewinding appropriately rearranges the second web-strip. As a result, the presentation order of the end shapes of the web-segments generated when unwinding the second web-strip can be the same as the presentation order of the end shapes of the web-segments generated when unwinding the first web-strip.

To address the problems and complexities that can arise from wound rolls of web-strips configured with longitudinally-asymmetric web-segments, a festooning of the web-strips can be employed. As representatively shown in FIGS. 3 and 3A, a selected web-strip 30 can be substantially continuously collected in a suitable container in the festooned configuration. For example, the separated storing of the first web-strip 30a can include a festooning of the first web-strip. Additionally, the separated storing of the second web-strip 30b can include a festooning of the second web-strip. In the festooned arrangement, the selected web-strip 30 can be laid in a back-and-forth arrangement which produces a plurality of interconnected layers of the web material.

A web-strip from an odd-numbered lane (e.g. web-strip 30a) can be festooned with a first end shape (A) of each web-segment leading the second end shape (B) of the web-segment into a storage supply, such as provided by a container 94. A web-strip from an even-numbered lane (e.g. web-strip 30b) can be festooned with the first end shape (A) of each web-segment trailing the second end shape (B) of the web-segment into a storage supply. With the festooned configuration, the presentation sequence of the web-segment end portions can be controlled by removing the web-strip from either the top or the bottom of the container, as appropriate. If the web-strip is removed from the top, the removal process is first-in, last-out, like conventionally wound rolls. If the web is removed from the bottom of the container, the removal process becomes first-in, first-out. Additionally, the removal of the web-strip from the bottom of the container can reverse the presentation sequence of the web-segment end portions, as compared to the presentation sequence provided by removing the web strip from top of the container. Accordingly, the festooning process can be more efficiently adjusted to provide a single, constant presentation sequence of different end shapes of the asymmetric web-segments.

With reference to FIG. 5, a web-strip having the desired presentation sequence of web-segment, end shapes (e.g. sequence A-B, A-B, . . . ; or B-A, B-A, . . . ) can be unwound or otherwise introduced to the longitudinal centerline of the process and apparatus to provide a base web 58. The base web can, for example, be put into motion by a surface or spindle driven unwind, or it could be pulled from a web supply by employing a driven nip or S-wrap. The motion of the base web can also be enhanced by the implementation of conventional vacuum conveyors. The use of 90-degree turn-bars may, however, impose excessive stress onto the absorbent base web. Additionally, it is desired that direction changes to align the base web to the centerline of the converting machine be kept to a minimum.

In the representatively shown example, the first contoured web-strip 30a can be delivered from first production supply 38 of contoured web-strip material. The first contoured web-strip 30a can present a primary production sequence of side edge contours 32 during the delivering of the first contoured web-strip 30a from the first production supply 38. The first contoured web-strip 30a has an appointed leading-end portion 46 and an appointed trailing-end portion 48.

At least a second contoured web-strip 30b can be delivered from a second production supply 40 of contoured web-strip material. The second contoured web-strip 30b is selectively configured to present the desired, primary production sequence of side edge contours during the delivering of the second contoured web-strip 30b from the second production supply 40. The first and second contoured web-strips 30a and 30b have been produced from a selected absorbent material. In a desired configuration, the first and second contoured web-strips can correspond to substantially adjacent web-strips which have been formed from the same web 22 of absorbent material. Alternatively, the first and second contoured web-strips can correspond to substantially non-adjacent web-strips which have been formed from the same web 22 of absorbent material. Optionally, the first and second contoured web-strips can correspond to web-strips which have been formed from different webs of the selected absorbent material.

Each production supply can include a festooned web-strip within a container 94 (e.g. FIGS. 3 and 3A). Each web-strip can have a first end portion which is first placed into the contained 94, and a second end portion which is last placed into the container.

As representatively shown in FIG. 5, the method and apparatus of the invention can include a transporting of the first contoured web-strip 30a to provide a moving base web 58. The base web can include an interconnected series of web-segments, and can be configured to substantially continuously provide a selected, primary production sequence of side edge contours. Additionally, the base web can be configured to substantially continuously provide a selected, primary production sequence of end shapes presented by the web-segments.

To provide the desired base web 58, the first contoured web-strip can be withdrawn from its corresponding container 94, or other supply system, on the basis of a selected sequence. For example, the selected sequence can be on the basis of last-end-in, first-end-out. Alternatively, the selected sequence may be on the basis of first-end-in, first-end-out.

In the representatively shown configuration, for example, the first production supply 38 of contoured web-strip material can be provided by a first festooned supply of the contoured web-strip material, and the first festooned supply may be configured to deliver the first contoured web-strip 30a on the basis of last-end-in, first-end-out. Alternatively, the first festooned supply may be configured to deliver the first contoured web-strip 30a on the basis of first-end-in, first-end-out. The delivery of the first contoured web-strip is suitably configured to provide the desired, primary production sequence of the side edge contours, and the desired, primary production sequence of the web-segment end shapes.

To provide the continuation of the selected, primary production sequence of side edge contours, the second contoured web-strip 30b can be withdrawn from the second production supply 40 on a suitable, cooperating basis. The cooperating basis is configured to provide a continuation of the desired, primary production sequence of the side edge contours, and the desired, primary production sequence of the web-segment end shapes.

The second production supply 40 of the contoured web-strip material can, for example, be provided by the representatively shown second festooned supply of the second contoured web-strip 30b. The second contoured web-strip 30b has been placed into its corresponding container 94 with a longitudinally-reversed orientation. The reversed orientation can present a different, substantially reversed sequence of side edge contours, as compared to the first contoured web-strip 30a that was placed into the first festooned supply of the first contoured web-strip.

To maintain the desired primary production sequence of side edge contours, the second contoured web-strip 30b can be withdrawn from the second festooned supply on a sequence which is reversed from the sequence upon which the first contoured web-strip 30a is withdrawn from the first festooned supply (e.g. FIGS. 3 and 3A). For example, where the first, festooned web-strip 30a is withdrawn on the sequence of last-in, first-out, the second festooned web-strip 30b can be withdrawn on the sequence of first-in, first-out. Alternatively, where the first, festooned web-strip 30a is withdrawn on the sequence of first-in, first-out, the second festooned web-strip 30b can be withdrawn on the sequence of last-in, first-out. Accordingly a splicing or other operative joining of the leading end portion 46 of the second contoured web-strip 30b to the trailing end portion 48 of the first contoured web-strip 30a can be operatively maintain the desired production sequence of segment-shapes and side edge contours in the interconnected, continuing base web 58. As representatively shown in FIG. 3A, the second web-strip 30b can be withdrawn from the "bottom" of its corresponding container. It should be readily appreciated that, for convenience, the illustrated container may be turned upside-down to allow an operative dispensing of the second web-strip 30b from the "top" of its container.

The base web 58 and other component webs can be appropriately guided through the desired manufacturing process with one or more operative guiding mechanisms 64. Various conventional web guide mechanisms can be employed to keep the various webs substantially aligned with a machine-direction centerline of the method and apparatus. For example, an absorbent web supplied on a roll can tend to take on a camber if the web is level-wound or processed in any way that bends the web in the cross-machine direction. An operative web guide can effectively counteract the effects of this camber. While any operative web guide may be employed, those that minimize the cross-directional bending of the absorbent web are preferred. For example, the web bending can be reduced by minimizing any wrapping of the absorbent web around an idler roll. Suitable web guides can, for example, include a camber roller Fife guide, which is available from the Fife Corporation, a business having offices located in Okla. City, Okla.

In the representatively shown configuration, the base web 58 can be delivered to a phasing accumulator device, the operation of which is well known in the art. Accordingly, the process and apparatus can include a selective accumulating of the moving base web 58 to accommodate a selective phasing of the base web. In a particular arrangement, the phasing accumulator 82 can change a path length of the base web 58 through the manufacturing process to selectively advance or retard a positioning of the base web 58 with respect to the relatively downstream processing mechanisms that are employed in the manufacturing line.

When introducing the periodically patterned base web 58 into the method and apparatus, the adjustment of the phasing or relative positioning of the base web (as compared to the appointed locations of other product components) can be important. The use of a base web that is non-phaseable, and the use of a base web that serves as a machine-reference to which other components are registered, can be cost-prohibitive. If such a configuration is employed, the positioning every component of the desired end-article would have to be re-phased after every splice of the web-strips employed to generate the base web. The defective-product waste created during the re-phasing operations can be significantly reduced by operatively advancing or retarding the shaped base web independently from the other article components. Accordingly, a desired feature of the invention can include a phasing mechanism and phasing operation which can operatively position each pre-shaped absorbent web-segment in a desired location within the article assembly. The phasing operation can desirably include a moving of the base web without inducing an excessive increase in tension that might break the base web. Various phasing systems may be employed. Examples of such phase-shifting systems are well known in the art, and are available from commercial vendors. As illustrated in the representatively shown configuration, the phasing mechanism can include an accumulator 82, and the accumulator can be configured to direct the base web along a path having one or more S-shaped, loop regions. The sizes of the loop regions can be varied to control the positioning and phasing of the base web with respect to a selected reference in any conventional manner. In a particular aspect, the accumulator can decreases its loop size to advance the absorbent, and increases the loop size to retard the absorbent.

Additionally, the method and apparatus can also include a compressing of the base web 58 to reduce its thickness. The compressing may also increase the density of the base web, and may increase the longitudinal length and/or the cross-directional width of the web. The compressing may be substantially uniformly or non-uniformly applied across the surface of the base web. Additionally, the compressing can be configured to emboss a desired pattern of embossments along the machine-direction and/or cross-direction. As representatively shown, the compressing of the base web can be provided by a counter-rotating pair of nip rollers 84. Alternative compressing devices or systems can include converging gap rollers, converging gap conveyor belts or the like, as well as combinations thereof.

The absorbent components and materials employed with the present invention may be compressed and debulked by employing an operation that is located on-line, off-line or both. While it may be less expensive to have the absorbent material delivered to the converting machine at a desired, final density, an on-line density control can offer product and process advantages. The debulking can more effectively control the stiffness and/or thickness of the compressed absorbent material, and can reduce the variability of the thickness. The controlled thickness can, for example, help to ensure a more consistent stacking and packaging of the final articles. The on-line debulking can also help to remove any creases in the absorbent material that may have been induced by storing the absorbent material in a festooned condition. The effectiveness of the crease-removal can be improved by heating the debulking roll. A significant difficulty in processing festooned material is the difficulty of dealing with disruptive bending waves that can be induced by the festooning switchbacks. An operation of a heated debulking system can reduce the process upsets that can be caused by the festooning switchbacks. When employing a heated debulker system, the heat imparted into the web should be less than that required for melting and resetting the binder fibers in the absorbent web material. The debulking rolls may have substantially flat surfaces or may have textured or contoured surfaces that may include an embossing pattern.

In a particular feature, an optional first tissue layer 54 may be assembled to the base web 58. In a desired configuration, a bonding device such as provided by a adhesive applicator 62 may be employed to secure the first tissue layer 54 to the base web 58.

Another aspect of the invention can include a joining of at least one supplemental layer of absorbent material onto a major surface of the base web 58. Optionally, a plurality of supplemental layers may be joined to the base web. In the representatively shown configuration, for example, the supplemental layer can be provided by the illustrated pledgets 50. In a particular arrangement, a pledget of absorbent material may be added to each appointed web-segment. The machine-directional length of each pledget may be substantially equal to the full length of its associated, corresponding web-segment, or shorter than the associated web-segment. For the full-length configuration, the web of pledget material may be unwound at the same pitch as the base web 58, joined to the base web, and then cut to length at the same time that the base web is separated at the ends of the individual, appointed web-segments by an operative, pad cutoff mechanism. The cross-directional width of each pledget can be less than the smallest width dimension of its associated, corresponding web-segment. The width of each pledget can alternatively equal to, or greater than the width of the smallest width dimension of the corresponding web-segment.

To reduce the cost of material, the pledget can be configured to have a longitudinal, machine-direction length which is shorter than the length of the pledget's corresponding web-segment. While various cut-and-place module designs are may be employed, those that have a speed-matching capability are desired. Suitable modules are well known in the art and are available from commercial vendors; such as Curt G. Joa, Inc., a business having offices located in Sheboygan Falls, Wis., and the Paper Converting Machine Company, a business having offices located in Green Bay, Wis. If a sufficient speed-matching of the two elements is not achieved, cyclical shock loads can be imparted into the absorbent base web, and the shock loads can generate excessive registration drifts, and cause defective products. The shock loadings may also break or otherwise damage the physical integrity of the absorbent base web.

In another aspect, the invention can include a configuring of the at least one supplemental layer of absorbent material with an absorbent capacity of at least about 8 g/g of 0.9 wt % saline. In a further aspect, the invention can include a joining of a plurality of individual, separately provided, spaced-apart, absorbent pledget members 50 onto a major surface of the base web 58. Each of the absorbent pledget members 50 has a longitudinal length which is less than the longitudinal length of its corresponding web segment 88 of the base web 58. Each of the absorbent pledget members can also be configured with an absorbent capacity which is at least about 8 g/g of saline. Additionally, each of the absorbent pledget members 50 can have an absorbent capacity of up to about 50 g/g, or more, to provide improved performance.

A suitable pledget web 51 can be delivered from an operative pledget supply 52 and suitably transported by an operative conveyor. An operative pledget cutter device 60 can be employed to separate the pledget web 51 into a plurality of individual pledgets 50 can be selectively placed onto the base web 58 at appointed locations along the base web. As representatively shown, the individual pledgets can be positioned at locations that are spaced apart along the longitudinal direction 24 of the base web 58. In a particular aspect, the base web 58 can represent an interconnected plurality of appointed web segments 88, and the pledgets 50 can be allocated with one pledget per web segment 88 of the base web 58. In a particular feature, an operative securing mechanism, such as provided by an adhesive applicator 66, may be employed to operatively attach the individual pledgets 50 to the moving base web 58.

The use of one or more tissue layers or other supplemental, porous substrates can help strengthen the absorbent base web, and help contain fiber and superabsorbent material. The substrate(s) can be a single support layer, top and bottom support layers, or a single layer which is folded to envelop all or part of the absorbent web. The substrate is desirably introduced into the process as soon as possible to maximize the containment time. The incorporation of the supplemental layer(s) can help reduce the shake-out loss of material, reduce dust, reduce costs, and improve housekeeping.

The resulting base web 58 and assembled components can then be subjected to subsequent processing operations. For example, a system of folding boards 68 may be employed to wrap a selected layer of material around the absorbent pad, or to form additional plies or layers of selected materials.

Additionally the base web 58 and assembled components may be processed by a system of assembly nip rollers 70, which can enhance the desired attachments between the assembled components. The resulting composite base web can then be separated into individual absorbent assemblies 98 by employing a suitable cutter mechanism, such as provided by the representatively shown cutter device 86.

The absorbent assemblies 98 can be further combined with other components, as desired. For example, the absorbent assemblies 98 may be laminated to a layer of liner materials 74 which is provided from a suitable liner supply 76. Additionally, the absorbent assemblies 98 may be combined with a layer of outer cover material 78, which is provided from a suitable outer cover supply 80. As representatively shown, the absorbent assemblies 98 may be sandwiched between the liner layer 74 and the outer cover layer 78, as desired.

In the various attachments and securements employed in the constructions of the method and apparatus of the invention, it should be readily apparent that any conventional attachment or securement technique may be employed. Such techniques may, for example, include adhesives, stitches, welds, screws, bolts, rivets, pins, latches, clamps or the like, as well as combinations thereof.

Similarly, it should be readily apparent that any conventional material may be employed to construct the various components incorporated into the method and apparatus of the invention. Such materials can include synthetic polymers, fiberglass-resin composites, carbon fiber-resin composites, metals, metallic composites, ceramic composites, and the like, as well as combinations thereof. The materials are typically selected to provide desired levels of strength, durability, ease of manufacture, and ease of maintenance.

Although various illustrative and representative configurations have been described in detail herein, it is to be appreciated that other variants, modifications and arrangements are possible. All of such variations, modifications and arrangements are to be considered as being within the scope of the present invention.

What is claimed is:

1. A method for making an absorbent article, said method including:
    a providing of a web of absorbent material;
    a dividing of said web to provide at least two web-strips having a substantially nested relation, each said web-strip having a pair of laterally opposed, contoured side edges with alternating, concave and convex side edge portions;
    a configuring of a first web-strip to provide a first orientation which presents a first sequence of side edge contours;
    a configuring of at least a second web-strip to provide a longitudinally reversed orientation which presents a different, substantially reversed sequence of side edge contours;
    a separated storing of said web-strips to provide a first production supply of contoured web-strip material, and at least a second production supply of contoured web-strip material;
    a delivering of said first contoured web-strip from said first production supply of contoured web-strip material, said first contoured web-strip presenting a primary production sequence of side edge contours during the delivering of said first contoured web-strip;
    a delivering of at least said second contoured web-strip from said second production supply of contoured web-strip material, said second contoured web-strip presenting said primary production sequence of side edge contours during the delivering of said second contoured web-strip.

2. A method as recited in claim 1, further including an operative joining of a leading-end portion of said second contoured web-strip to a trailing-end portion said first contoured web-strip to provide a continuing base web.

3. A method as recited in claim 1, wherein said concave side edge portions have been configured to be non-symmetric with respect to a longitudinal direction of said base web.

4. A method as recited in claim 3, wherein said convex side edge portions have been configured to be non-symmetric with respect to said longitudinal direction of said base web.

5. A method as recited in claim 1, wherein the storing of said first web-strip includes a festooning of said first web-strip.

6. A method as recited in claim 1, wherein the storing of said first web-strip includes a spiral winding of said first web-strip.

7. A method as recited in claim 1, wherein the storing of said second web-strip includes a festooning of said second web-strip.

8. A method as recited in claim 1, wherein the storing of said second web-strip includes a preliminary, spiral winding of said second web-strip; and a subsequent spiral re-winding of said second web-strip to thereby provide said second production supply of web material.

9. A method as recited in claim 1, wherein said web of absorbent material has been provided with a tensile strength of at least a minimum of about 1 N/cm.

10. A method as recited in claim 1, further including a transporting of said first contoured web-strip to provide a moving base web.

11. A method as recited in claim 10, further including a joining of at least one supplemental layer of absorbent material onto a major surface of said base web.

12. A method for making an absorbent article, said method including:
    a delivering of a first contoured web-strip from a first production supply of contoured web-strip material, said first contoured web-strip presenting a primary production sequence of side edge contours during the delivering of said first contoured web-strip; and
    a delivering of at least a second contoured web-strip from a second production supply of contoured web-strip material, said second contoured web-strip also presenting said primary production sequence of side edge contours during the delivering of said second contoured web-strip;
    wherein
        said first and second contoured web-strips have been produced from a web of absorbent material;

said web of absorbent material has been divided to provide at least two web-strips having a substantially nested configuration, each said web-strip having a pair of laterally opposed, contoured side edges with alternating, concave and convex side edge portions;

a first web-strip has been configured to provide a first orientation which presents a first sequence of side edge contours in said first production supply;

at least a second web-strip has been configured to provide a longitudinally reversed orientation which presents a different, substantially reversed sequence of side edge contours in said second production supply; and said web-strips have been separately stored to provide said first production supply of contoured web-strip material, and at least said second production supply of contoured web-strip material.

13. A method as recited in claim 12, further including an operative joining of a leading-end portion of said second contoured web-strip to a trailing-end portion said first contoured web-strip to provide a continuing base web.

14. A method as recited in claim 12, wherein said concave side edge portions have been configured to be non-symmetric with respect to a longitudinal direction of said base web.

15. A method as recited in claim 14, wherein said convex side edge portions have been configured to be non-symmetric with respect to said longitudinal direction of said base web.

16. A method as recited in claim 12, wherein said first web-strip has been stored by a festooning of said first web-strip.

17. A method as recited in claim 12, wherein said first web-strip has been stored by a spiral winding of said first web-strip.

18. A method as recited in claim 12, wherein said second web-strip has been stored by a festooning of said second web-strip.

19. A method as recited in claim 12, wherein said second web-strip has been stored by a preliminary, spiral winding of said second web-strip; and a subsequent spiral re-winding of said second web-strip to thereby provide said second production supply of web material.

20. A method for making an absorbent article, said method including:

a delivering of a first contoured web-strip from a first production supply of contoured web-strip material, said first contoured web-strip presenting a primary production sequence of side edge contours during the delivering of said first contoured web-strip;

a delivering of at least a second contoured web-strip from a second production supply of contoured web-strip material, said second contoured web-strip also presenting said primary production sequence of side edge contours during the delivering of said second contoured web-strip;

an operative joining of a leading-end portion of said second contoured web-strip to a trailing-end portion said first contoured web-strip to provide a continuing base web; and a joining of a plurality of pledget members of absorbent material onto a major surface of said base web;

wherein
said first and second contoured web-strips have been produced from a web of absorbent material;

said web of absorbent material has been divided to provide at least two web-strips having a substantially nested configuration, each said web-strip having a pair of laterally opposed, contoured side edges with alternating, concave and convex side edge portions;

said concave side edge portions have been configured to be non-symmetric with respect to a longitudinal direction of said base web;

a first web-strip has been configured to provide a first orientation which presents a first sequence of side edge contours in said first production supply;

at least a second web-strip has been configured to provide a longitudinally reversed orientation which presents a different, substantially reversed sequence of side edge contours in said second production supply; and said web-strips have been separately stored to provide said first production supply of contoured web-strip material, and at least said second production supply of contoured web-strip material.

* * * * *